United States Patent [19]

Plischke et al.

[11] Patent Number: 5,079,063
[45] Date of Patent: Jan. 7, 1992

[54] SOLUTION-SPUN ANTIFLEA FIBERS

[75] Inventors: Le Moyne W. Plischke, Lillian, Ala.; Rupert J. Snooks, Jr., Gulf Breeze; Scott E. Osborn, Cantonment, both of Fla.

[73] Assignee: Monsanto Company, St. Louis, Mo.

[21] Appl. No.: 721,075

[22] Filed: Jun. 21, 1991

Related U.S. Application Data

[63] Continuation-in-part of Ser. No. 289,145, Dec. 23, 1988, Pat. No. 5,028,471.

[51] Int. Cl.⁵ .................................................. B32B 3/02
[52] U.S. Cl. .................................... 428/95; 424/403; 514/875; 523/122; 428/85; 428/97; 428/297; 428/364; 428/392; 428/394
[58] Field of Search .................... 424/403; 514/875; 523/122; 428/85, 95, 97, 297, 364, 392, 394

[56] References Cited

U.S. PATENT DOCUMENTS 4,379,168  4/1983  Dotolo ............................. 424/356
4,961,930  10/1990  Perdelwitz et al. ............... 428/288

OTHER PUBLICATIONS

W. E. Taylor et al., Ghana Jnl Argic. Sci. 7, 61-62 (1974), Insecticidal Properties of Limonene, a Constituant of Citrus Oil.
S. B. Hooser et al., Javma, vol. 189, No. 8 (Oct. 15, 1986).
Jeff Cox, Organic Gardening, p. 136, Mar. 1984, Discoveries Oil from Citrus Skins is Potent Insecticide.
Chemical Week, Jun. 27, 1984, Squeezing Insecticides from Oranges.

Primary Examiner—James J. Bell
Attorney, Agent, or Firm—John W. Whisler

[57] ABSTRACT

Fibers having a substance incorporated therein to kill fleas are described. Fabrics (e.g. carpet and socks) containing these fibers are useful for ridding households and household pets of fleas.

13 Claims, No Drawings

SOLUTION-SPUN ANTIFLEA FIBERS

This application is a continuation-in-part of copending application Ser. No. 07/289,145, filed Dec. 23, 1988, now U.S. Pat. No. 5,028,471.

This invention relates to a simple and effective means for ridding households and household pets of the common flea (Ctenocephalides canis and felis).

Fleas are the Draculas of the insect world and are the leading cause of skin allergies in dogs and cats. Fleas also are often the carriers of serious diseases and parasites—like tapeworms—that can infect dogs and humans alike. Without a proper plan of attack the pet owner is certain to lose in the war against fleas. Fleas are hard to see and even harder to kill. The flea is slightly larger than 1/32 of an inch (0.08 cm) in length, is red, brown or black in color and is protected by a hard flat shell. The feet of a flea have double claws for catching hold of the pet's skin and fur in a pinching manner. Once attached to the pet, the flea has spine-like teeth that bite and cause inflammation of the pet's skin. The flea can leap 8 inches (20.3 cm) high and a distance of 12 inches (30.5 cm). One mating pair of fleas may, in their 274-day lifetime, be responsible for the creation of 250,000 fleas. Fleas spend only 10% to 20% of their life on the pet, the remainder is spent in the environment, be it in the yard or the house. Fleas can remain frozen for considerable periods of time and still thaw out and be as good as new. Once in the house, fleas become a year-around household problem. In fact, for the flea, a carpet is probably preferable to the yard. Fleas are primarily a parasite of household pets (dogs and cats). However, if all pets are removed from a household having fleas, the fleas will then attack humans.

Various chemical treatments, either of the pet or the pet's environment or both, have been recommended for the purpose of ridding the pet and its environment of the flea. The treatments include shampoos and dips for external application to the pet, medicines for internal application to the pet, and spraying and fogging for application to the pet's environment. Chemicals which have been used in conjunction with the treatments are well-known in the art and include terpenes (e.g. d-limonene), malathion, diazinon, and organophosphates. U.S. Pat. No. 4,379,168 describes pesticide compositions containing d-limonene along with surfactants or emulsifiers and water.

Such treatments, however, are only of a temporary nature. Moreover, care must be exercised in application of the chemicals to avoid irritation of the pet's skin. For example, the treatments are usually infrequent (e.g. shampoos being bi-weekly and dips being every six weeks).

Accordingly, there is a need in the art to provide a means for rescuing the homeowner and household pet from the common flea.

SUMMARY OF THE INVENTION

The present invention provides a simple, safe and effective means for ridding pets and households of the common flea. Specifically, the invention provides fibers characterized in having an antiflea agent incorporated therein and exposed at the fiber surface in an amount sufficient to control fleas which come into contact with the fiber. The term "fiber", as used herein, means fibers of continuous length (filaments) or of short length (staple) made therefrom.

The term "antiflea agent", as used herein, means a chemical substance which is a liquid and effective for controlling (i.e. killing or repelling) the common flea. The antiflea fibers of the invention are characterized in having a low concentration of the agent available at the fiber surface for immediate use in controlling fleas and additional agent beneath the fiber surface for future use in controlling fleas. Thus, as agent is lost from the fiber surface with time for whatever reason, fresh agent migrates to the fiber surface to take its place. In effect, the antiflea agent is "time-released" from the fiber. In this manner, the concentration of the agent may be maintained at a safe level, there is no obnoxious odors associated with the agent, and the flea protection is of a relatively permanent nature. These results are not obtained if the agent, instead of being incorporated into the fibers, is merely present as a surface coating on the fibers.

DETAILED DESCRIPTION OF THE PREFERRED EMBODIMENTS OF THE INVENTION

The antiflea fibers of the invention are prepared in filament form and may be melt spun from polyolefins (e.g. propylene), nylon (e.g. nylon 66 and nylon 6) or polyesters (e.g. polyethylene terephthalate) or solution spun (sometimes referred to as wet spun) from, for example, a solution of an acrylic or modacrylic polymer, or rayon or nylon in an appropriate solvent. When preparing the filaments by solution spinning of acrylic or modacrylic filaments, the antiflea agent is preferably incorporated into the filaments at a point in the process at which the filaments still have a very open and porous structure. The preparation of acrylic fibers, including the solution spinning of acrylic tow, is well-known in the art, for example see Encyclopedia of Polymer Science and Engineering, Volume 1, Second Edition, pages 334-388 (Acrylic Fibers), published by John Wiley & Sons, Inc. (1985). In the solution spinning of acrylic tow, a dope (solution of the acrylic polymer in an appropriate solvent) is extruded through a spinneret immersed in a bath (coagulation bath) containing a mixture of solvent and nonsolvent (e.g. water) to provide tow of filaments which is: withdrawn from the bath; washed to remove solvent; stretched in hot water (wet stretched); passed through a finish bath to apply a finish thereto in order to provide surface lubrication for further processing of the tow and to prevent static buildup of the tow; and, then, passed over heated rolls (drying rolls) to dry the filaments and collapse the pores and voids. (Optionally, the filaments may be hot-stretched on the drying rolls to create a desirable tensile property profile and/or reduce the diameter, i.e., denier or tex, of the filaments for purposes of end use applications. The tow is advance during the spinning process by means of rolls, the peripheral speeds of which are selected to control the speed of and tension (including stretching) in the tow. Preferably, the antiflea agent is applied to the filaments from the finish bath through which the filaments pass enroute to the drying rolls. When the filaments are then processed on the drying rolls, the antiflea agent is retained inside the fiber. After being dried and collapsed, the tow is crimped, annealed with steam under pressure to make the filaments less brittle, optionally, crimped a second time (recrimped) and, then, usually cut into staple and baled. Instead of applying the antiflea agent to the tow from the spin finish, the agent may be applied to the tow as a spray or foam just prior to the crimping or recrimping step. The staple is then converted into yarn and used to make textile fabrics and carpets in conventional manner. After the antiflea agent is applied to the tow, care is taken, that is, conditions are selected so as not to volatilize the antiflea agents during subsequent processing of the tow.

Acrylic polymers of particular commercial importance are those comprising acrylonitrile units and either vinyl acetate, methacrylate or methyl methacrylate units. Optionally, the polymers may also contain vinyl bromide units to impart flame resistance to the polymers. Modacrylic polymers of particular commercial importance are those comprising acrylonitrile, vinylidene chloride and/or vinyl bromide units.

When preparing the filaments by melt spinning, the antiflea agent is preferably incorporated into the filaments by applying the agent to the filaments either prior to or along with spin finish application. When applied prior to spin finish application, the agent is preferably applied from an aqueous emulsion thereof. Spin finish containing agent may be applied to the filaments in a conventional manner, for example, by passing the filaments over a metered finish applicator where a predetermined amount of finish is applied to the filaments and the filaments converged to form a yarn. The yarn normally is then either drawn and collected or collected and drawn in a separate operation. Alternatively, the agents may be incorporated into the polymer from which the filaments are melt-spun, for example, by adding the agent to the molten polymer just prior to melt-spinning of the filaments. The filaments or staple cut therefrom may be used in a conventional manner to make carpets and other fabrics.

A particularly preferred antiflea agent for use in practicing the present invention is d-limonen which is a terpene. Other effective terpenes are pinen, cincole, carvone, phellandrene and terpineol. d-Limonene, which is the major constituent of citrus oils, is known to be effective in controlling insects, including fleas, is inexpensive, abundant and is reported to be non-toxic to both pets and humans.

The concentration of the antiflea agent in the fiber may vary over a wide range depending on the particular agent employed and the particular intended end use application for the fibers.

The fibers of the present invention are particularly useful for making flea-free carpet and cloth (e.g. sock) that may be strategically placed in the household, for example, in the dog's or cat's bed. The flea-free carpet may, for example, be used in the form of wall-to-wall carpet or area rugs that protects the pet and entire household from fleas or it may also be used in the form of a pad on which the pet sleeps or rests. In constructing the flea-free carpet, the fibers of the invention may be used as pile fibers or as "grin cover" fibers. Grin cover fibers cover the upper surface of the primary backing of cut pile carpet and is exposed when the pile fibers fail, for whatever reason, to completely cover the primary backing. Typically, grin cover fibers are of the same chemical composition fiber as the pile fibers and are needle punched into the primary backing. When the carpet is dyed, the grin cover fibers and pile fibers are dyed to the same shade of color.

The following example is given for the purpose of further illustrating the invention and is not intended in any way to limit the scope of the invention to the particular materials described herein. In the examples, percentages are by weight unless otherwise specified.

EXAMPLE 20

This example illustrates preparation of melt spun fibers of the present invention and their utility in controlling fleas.

Nylon 66 polymer of fiber-forming grade is melt-spun into 4080 denier, 68 filament carpet yarn in a conventional matter. During melt spinning, the filaments, after being quenched, are passed over a conventional metered finish applicator where the filaments are converged to form a yarn and where a sufficient amount of a solution consisting of 60% d-limonene and 40% emulsifier (Tween®20) is applied to the yarn to provide filaments having 1.8% by weight of d-limonene incorporated therein. The yarn is then passed through a conventional steam conditioning tube measuring about 1.8 meters in length where the yarn is treated with steam to facilitate subsequent collection of the yarn. The yarn is then passed over a conventional metered finish applicator where an aqueous spin finish containing a lubricant is applied to the yarn. The yarn is then passed over and around a driven feed roll and its associated separator roll with several wraps and finally collected on a bobbin. A sufficient amount of a solution consisting of 60% d-limonene and 40% emulsifier (Tween®20) is applied to the filaments after convergence and before steam conditioning to provide filaments having 1.8% d-limonene on weight of fiber (o.w.f.) incorporated therein. The as-spun yarn is then drawn to a denier of 1340, textured and tufted into cut-pile carpet.

In one experiment, a square carpet sample measuring 150 mm × 150 mm is placed pile side up in a cylindrical glass container having a diameter of 175 mm, a height of 75 mm and being open at one end. Ten fleas are removed from a four-year old black female pug and placed in the container. The open end of the container is covered with a fine woven nylon fabric and the fabric secured to the container by means of rubber bands. The fabric prevents the fleas from escaping while allowing fresh air to circulate in the container. After a period of 24 hours, all of the fleas are dead.

In a second experiment, the first experiment is repeated, except in this instance the antiflea agent is omitted from the carpet sample. After a period of 24 hours, all of the fleas are still active.

The above experiments show that the fibers of the present invention provide is a simple, economical and effective means for ridding households and household pets of fleas that otherwise infest households and torment and even kill household pets.

EXAMPLE 2

This example illustrates the preparation of solution-spun fibers of the present invention.

An acrylic polymer consisting of 92.5% by weight of acrylonitrile units and 7.5% by weight of vinylacetate is dissolved in dimethylacetamide (DMAc) in an amount sufficient to provide a 25% by weight polymer solution (dope). The dope, at a temperature of 105° C., is extruded through a spinnerette having 15,000 orifices. The spinnerette is immersed in an aqueous DMAc coagulation bath having a DMAc concentration of 55% by weight with water being added during spinning to maintain this concentration. The temperature of the bath is maintained at 40° C. The resulting filament bundle (tow) is withdrawn from the bath, washed with water to remove DMAc, passed through an aqueous bath containing cationic dye to impart color thereto and stretched six times (6X) its length in a 90° C. hot water bath to provide 10 denier filaments. The tow is passed form the hot water bath through a finish bath comprising lubricant and sufficient d-limonene so as to apply to the filaments 1.8% by weight of d-limonene, based on the weight of the filaments. The filaments at this point in the process have a very open and porous structure. The tow is passed from the finish bath over heated rolls on which the tow is dried and the pores and voids in the filaments are collapsed. The 10 dpf tow is then crimped (stuffer box crimped using steam), annealed under pressure with steam, recrimped, and cut into 4¼ inch staple. During annealing the filaments shrink causing the dpt to increase from 10 to 15 dpf. This staple is then processed in a conventional manner into an appropriate yarn for knitting socks, making carpet or other textile articles. Instead of using the above acrylic polymer, a modacrylic polymer, for example, a polymer containing 64% by weight of acrylonitrile units, 12% by weight of vinyl bromide units and 24% by weight of vinylidene chloride units.

Although the specification has been directed to using the fibers of the present invention to control fleas, it will be understood that the antiflea agent will also control other insects, for example, d-limonene will control ants and fleas. The particular insects, in addition to fleas, which can be controlled by application of the fibers of the invention will, of course, depend on the particular antiflea agent incorporated into the fibers and the concentration thereof.

What is claimed is:

1. A fiber selected from the group consisting of solution-spun filaments characterized in having an antiflea agent incorporated therein and exposed at the surface thereof in an amount sufficient to control fleas which come into contact therewith and staple length fibers made from said filaments.

2. The fiber of claim 1 wherein said fiber is an acrylic or modacrylic fiber.

3. The fiber of claim 2 wherein said antiflea agent is a terpene.

4. The fiber of claim 3 wherein said terpene is d-limonene.

5. A yarn consisting essentially of fibers of claim 4.

6. The yarn of claim 5 wherein said fibers are staple length fibers.

7. A cloth made from the yarn of claim 5.

8. A flea-free carpet comprising a primary backing having pile fibers attached thereto characterized in that said pile fibers comprise fibers selected from the group consisting of solution-spun filaments having an antiflea agent incorporated therein and exposed at the surface thereof in an amount sufficient to control fleas which come into contact therewith and staple length fibers made from said filaments.

9. A flea-free carpet comprising a primary backing having grin cover fibers and pile fibers attached thereto characterized in that said grin cover fibers comprise fibers selected from the group consisting of solution-spun filaments having an antiflea agent incorporated therein and exposed at the surface thereof in an amount sufficient to control fleas which come into contact therewith and staple length fibers made from said filaments.

10. The flea-free carpet of claim 8 wherein said antiflea agent is d-limonene.

11. The flea-free carpet of claim 9 wherein said antiflea agent is d-limonene.

12. The flea-free carpet of claim 10 wherein said pile fibers are acrylic or modacrylic fibers.

13. The flea-free carpet of claim 11 wherein said pile fibers and said grin cover fibers are acrylic or modacrylic fibers.

* * * * *